(12) United States Patent
Hyde et al.

(10) Patent No.: US 8,308,741 B2
(45) Date of Patent: Nov. 13, 2012

(54) SYSTEMS AND METHODS FOR AUTOMATICALLY INSERTING A NEEDLE INTO A LIVING SUBJECT

(75) Inventors: Roderick A. Hyde, Redmond, WA (US); Muriel Y. Ishikawa, Livermore, CA (US); Jordin T. Kare, Seattle, WA (US); Eric C. Leuthardt, St. Louis, MO (US); Michael A. Smith, Phoenix, AZ (US); Leif T. Stordal, Issaquah, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 620 days.

(21) Appl. No.: 12/387,150

(22) Filed: Apr. 28, 2009

(65) Prior Publication Data

US 2010/0274202 A1    Oct. 28, 2010

(51) Int. Cl.
*A61B 19/00* (2006.01)
*A61B 17/32* (2006.01)
*A61B 8/00* (2006.01)
*A61B 5/00* (2006.01)
*B65D 81/00* (2006.01)
*A61D 5/00* (2006.01)
*A61N 1/30* (2006.01)
*A61M 5/00* (2006.01)

(52) U.S. Cl. ........ 606/130; 600/461; 600/573; 600/576; 600/579; 600/581; 604/20; 604/21; 604/173; 606/167; 606/172

(58) Field of Classification Search ................. 600/573, 600/576, 578, 579, 581, 583, 584, 461; 604/19–22, 604/173; 606/108, 130, 167, 172
See application file for complete search history.

(56) References Cited

U.S. PATENT DOCUMENTS

| | | | |
|---|---|---|---|
| 4,527,569 A | 7/1985 | Kolb | |
| 4,817,622 A | 4/1989 | Pennypacker et al. | |
| 5,519,208 A | 5/1996 | Esparza et al. | |
| 5,969,754 A | 10/1999 | Zeman | |
| 6,068,599 A | 5/2000 | Saito et al. | |

(Continued)

FOREIGN PATENT DOCUMENTS

WO    WO 2009023798 A2  *  2/2009

*Primary Examiner* — Jeffrey G Hoekstra
*Assistant Examiner* — Devin Henson
(74) *Attorney, Agent, or Firm* — Workman Nydegger

(57) ABSTRACT

Embodiments disclosed herein are directed to systems and methods for automatically inserting a needle into an insertion-target region of a living subject in response to a machine-vision system locating the insertion-target region. In an embodiment, a needle insertion system includes a moveable needle configured to be inserted into a living subject, a machine-vision system configured to locate an insertion-target region of the living subject, control electrical circuitry, and an actuator coupled to the control electrical circuitry. The control electrical circuitry may be coupled to the machine-vision system to receive location information therefrom about the insertion-target region, and configured to output needle targeting instructions. The actuator may be coupled to the control electrical circuitry to receive the needle targeting instructions therefrom and coupled to the moveable needle. The actuator may be configured to move the moveable needle to the insertion-target region automatically in response to receiving the needle targeting instructions from the control electrical circuitry.

50 Claims, 9 Drawing Sheets

U.S. PATENT DOCUMENTS

| | | |
|---|---|---|
| 6,132,379 A | 10/2000 | Patacsil et al. |
| 6,230,046 B1 | 5/2001 | Crane et al. |
| 6,546,279 B1 * | 4/2003 | Bova et al. .................... 600/429 |
| 6,556,858 B1 | 4/2003 | Zeman |
| 7,527,593 B2 * | 5/2009 | Fidel et al. .................... 600/461 |
| 2004/0171923 A1 | 9/2004 | Kalafut et al. |
| 2005/0209564 A1 | 9/2005 | Bonner et al. |
| 2006/0184029 A1 | 8/2006 | Haim et al. |
| 2008/0021329 A1 | 1/2008 | Wood et al. |
| 2008/0027317 A1 | 1/2008 | Wood et al. |
| 2009/0005687 A1 * | 1/2009 | Kawae .......................... 600/461 |
| 2010/0330589 A1 * | 12/2010 | Bahrami et al. ............... 435/7.9 |

* cited by examiner

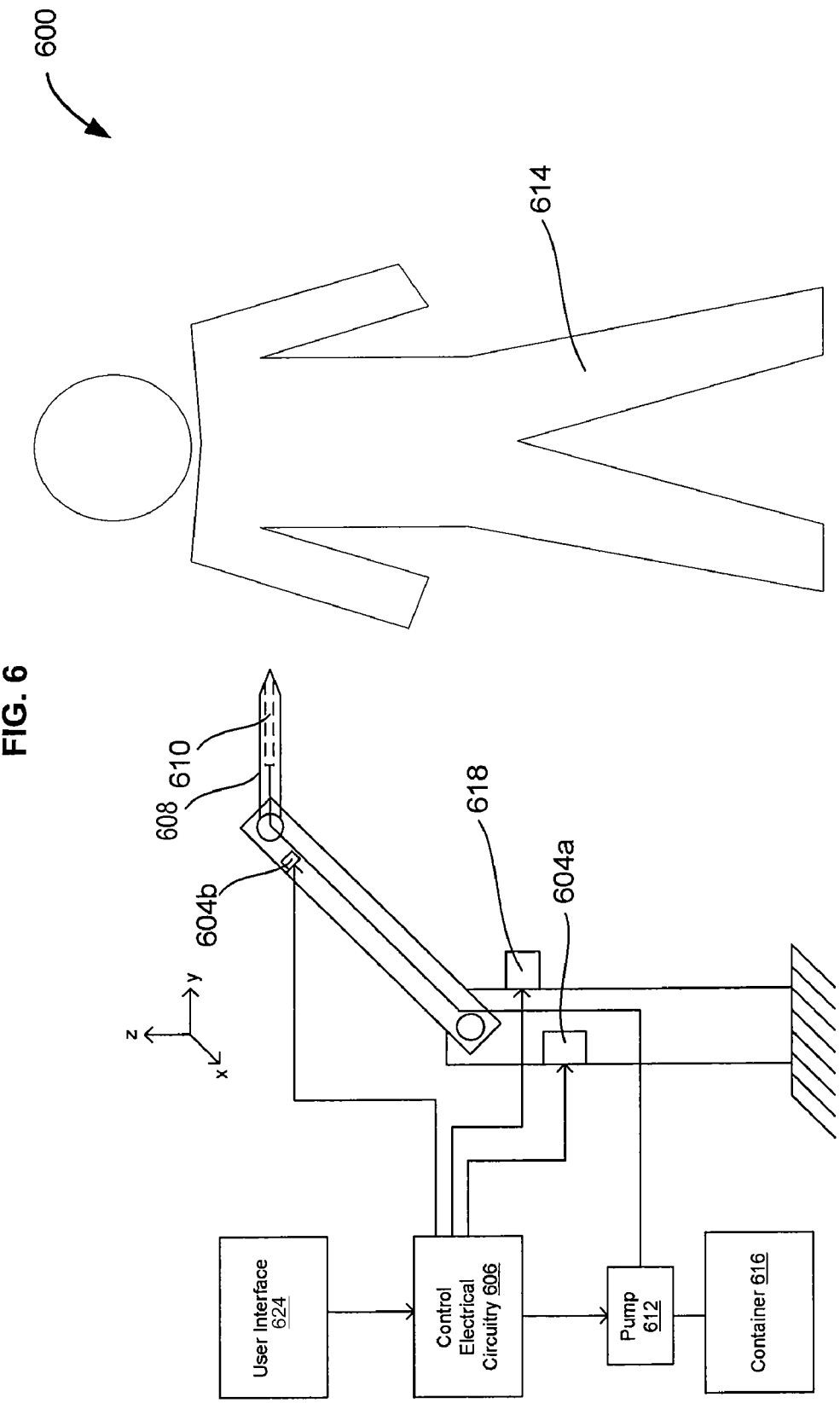

SYSTEMS AND METHODS FOR AUTOMATICALLY INSERTING A NEEDLE INTO A LIVING SUBJECT

SUMMARY

Embodiments disclosed herein are directed to systems and methods for automatically inserting a needle into an insertion-target region of a living subject in response to a machine-vision system locating the insertion-target region. In an embodiment, a needle insertion system includes a moveable needle configured to be inserted into a living subject, a machine-vision system configured to locate an insertion-target region of the living subject, control electrical circuitry, and an actuator coupled to the control electrical circuitry. The control electrical circuitry may be coupled to the machine-vision system to receive location information therefrom about the insertion-target region, and configured to output needle targeting instructions. The actuator may be coupled to the control electrical circuitry to receive the needle targeting instructions therefrom and coupled to the moveable needle. The actuator may be configured to move the moveable needle to the insertion-target region automatically in response to receiving the needle targeting instructions from the control electrical circuitry.

In an embodiment, a method of inserting a needle of a needle insertion system into a living subject is disclosed. The method includes locating an insertion-target region on the living subject with a machine-vision system. The method also includes outputting location information from the machine-vision system to control electrical circuitry. The method further includes automatically moving the needle to the insertion-target region in response to needle-targeting instructions output from the control electrical circuitry.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other living subject matter described herein will become apparent after reading the teachings set forth herein.

BRIEF DESCRIPTION OF THE FIGURES

FIG. 6 is schematic diagram of an embodiment of a needle insertion system in including a robotic arm having a moveable needle mounted thereto.

DETAILED DESCRIPTION

Figure 1A:
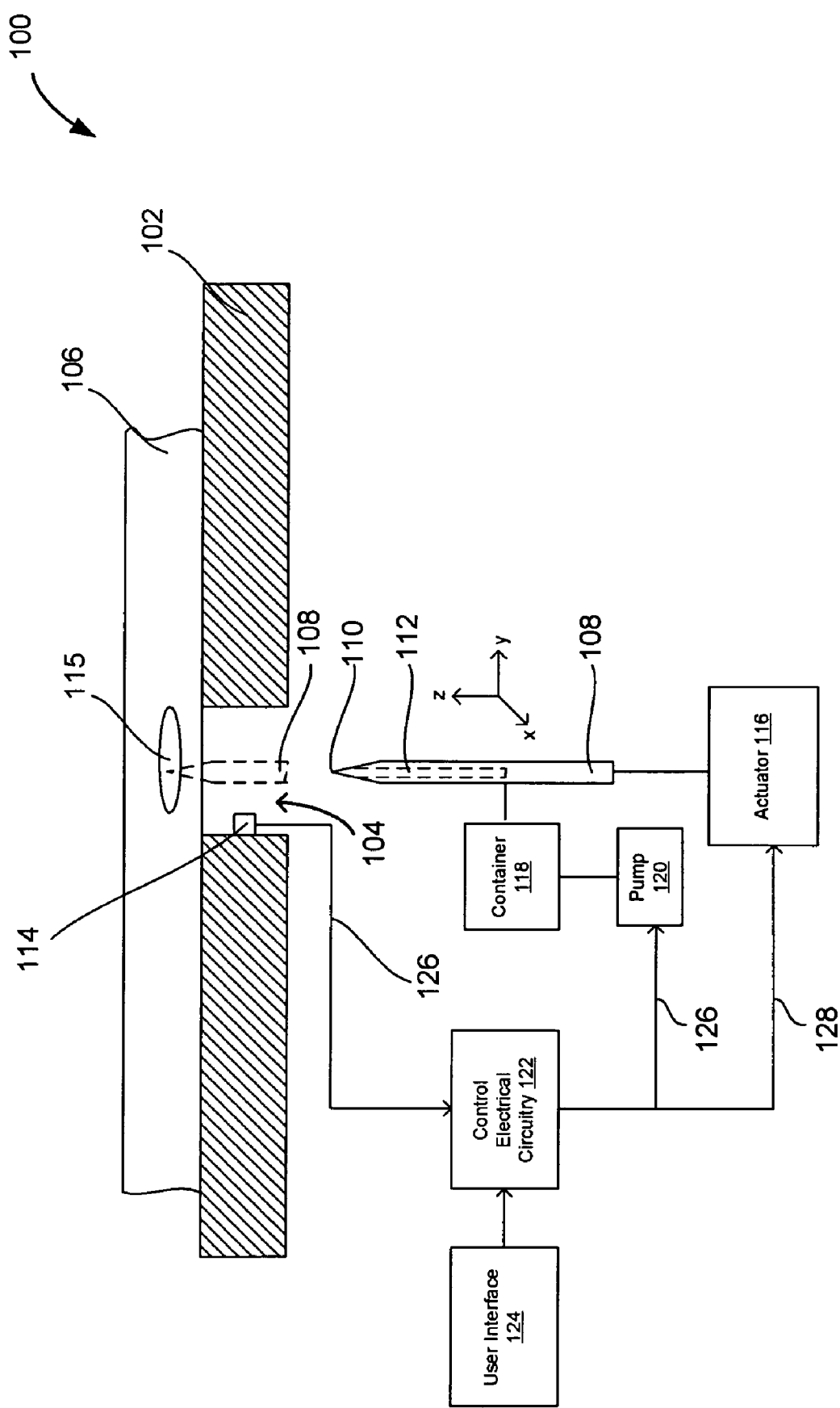
FIG. 1A is schematic diagram of an embodiment of a needle insertion system.

Embodiments disclosed herein are directed to systems and methods for automatically inserting a needle into an insertion-target region of a living subject in response to a machine-vision system locating the insertion-target region. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be strictly limiting. Other embodiments may be utilized, and other changes may be made, without departing from the spirit or scope of the subject matter presented herein.

FIG. 1A is schematic diagram of an embodiment of a needle insertion system 100. The needle insertion system 100 includes a support structure 102 (e.g., a table) having a through opening 104 extending therethrough that provides access to a body part 106 of a living subject (e.g., a human being) positioned on the support structure 102. The needle insertion system 100 further includes a moveable needle 108 having a sharp distal tip 110 configured to pierce tissue, muscle, or bone of the living subject. Thus, the moveable needle 108 may exhibit a variety of different needle geometries selected for a particular application. For example, the illustrated embodiment of the moveable needle 108 includes a passageway 112 (shown in phantom) that allows fluid to flow in and out of the sharp distal tip 110 of the moveable needle 108.

The needle insertion system 100 further includes a machine-vision system 114 positioned to have a field-of-view of the body part 106 through the through opening 104. The machine-vision system 114 is configured to locate a selected insertion-target region 115 of the body part 106 and distinguish specific regions and features of the body part 106, such as bone, muscle, or an artery (e.g., a vein or a blood vessel) from the insertion-target region 115. For example, the insertion-target region 115 may be bone, muscle, an artery, external tissue of the body part 106, or another selected external or internal region of the body part 106. The machine-vision system 114 may be an ultrasound imaging system, a thermal imaging system, an x-ray imaging device, an electronic camera, visual imaging, or another suitable machine-vision system.

The needle insertion system 100 also includes an actuator 116 that is operably coupled to the moveable needle 108. For example, the actuator 116 may be a pneumatic actuator, a hydraulic actuator, a piezoelectric actuator, a linear actuator, an electro-mechanical actuator, a shape-memory alloy actuator, or another suitable actuator. The actuator 116 is configured to selectively move the moveable needle 108 in and about x, y, and z axes in response to the machine-vision system 114 locating the insertion-target region 115.

The needle insertion system 100 may also include a container 118 in fluid communication with the passageway 112 formed in the moveable needle 108 and operably coupled to a pump 120 (e.g., a mechanical pump, an electro-mechanical pump) for pumping fluids into or out of the insertion-target region 115. In an embodiment, the container 118 may serve as a receptacle for fluids pumped out of the insertion-target region 115 of the living subject, such as blood or other bodily fluid.

Control electrical circuitry 122, along with a user interface 124 (e.g., a touchscreen, keypad, etc.) for user input, is provided. The control electrical circuitry 122 is operably coupled to the machine-vision system 114, the actuator 116, and the pump 120 to control the operation of the foregoing system components.

In operation, the machine-vision system 114 locates the insertion-target region 115 on the body part 106. One or more location-information signals 126 are output from the machine-vision system 114 to the control electrical circuitry 122 that encode location information about the insertion-target region 115. Automatically in response to the one or more location-information signals 126, the control electrical circuitry 122 outputs needle targeting instructions 128 to the actuator 116 without human intervention (e.g., without input from a user). Automatically and without human intervention, the actuator 116 moves the moveable needle 108 in accordance with the needle targeting instructions 128 so that the moveable needle 108 penetrates, for example, a blood vessel, tissue, muscle, or bone of the body part 106 and is inserted in the insertion-target region 115. The moveable needle 108 is shown in phantom inserted into the insertion-target region.

In an embodiment, the machine-vision system 114 may be configured to distinguish between external locations of the body part 106 that have been previously punctured by the moveable needle 108 or another needle, and locate (if available) a region of the body part 106 that is free of punctures and has not been penetrated (within a predetermined time period of, for example, 2 weeks) by the moveable needle 108 or another needle. Such an embodiment may help alleviate discomfort in the living subject associated with multiple needle penetration into the same insertion-target region or a region near a previous insertion-target region.

In an embodiment, the control electrical circuitry 122 may be configured to correlate anatomical information viewed by and received from the machine-vision system 114 with known anatomical data about the living subject. For example, the known anatomical data may be determined from at least one of ultrasound imaging, x-ray imaging, magnetic resonance imaging, infrared imaging, or a computed tomography scan of the living subject.

In an embodiment, the control electrical circuitry 122 may also output pumping instructions 130 to the pump 120 to pump bodily fluid from the insertion-target region 115 through the passageway 112 of the moveable needle 108 and into the container 118. Thus, in such an embodiment, the pump 120 may function as a suction device and the needle insertion system 100 may serve as a phlebotomy device for drawing blood from an artery or a biopsy needle system for taking a sample from the insertion-target region 115 for subsequent biopsy. For example, the moveable needle 108, container 118, and pump 120 may form all or part of a syringe device in which a plunger driven by an actuator controlled by the control electrical circuitry 122 functions as the pump 120.

In an embodiment, the control electrical circuitry 122 may be configured (e.g., programmed) with a plurality of different force settings that are user selectable via the user interface 124. In such an embodiment, the actuator 116 drives the moveable needle 108 with a force corresponding to a selected one of the plurality of different force settings selected via the user interface 124.

In an embodiment, the control electrical circuitry 122 may also output pumping instructions to the pump 120 to pump a fluid from the container 118 to the insertion-target region 115. For example, one or more drugs may be injected into the insertion-target region 115 as opposed to the pump 120 being used to draw fluid (e.g., blood) from the insertion-target region 115.

Figure 1B:
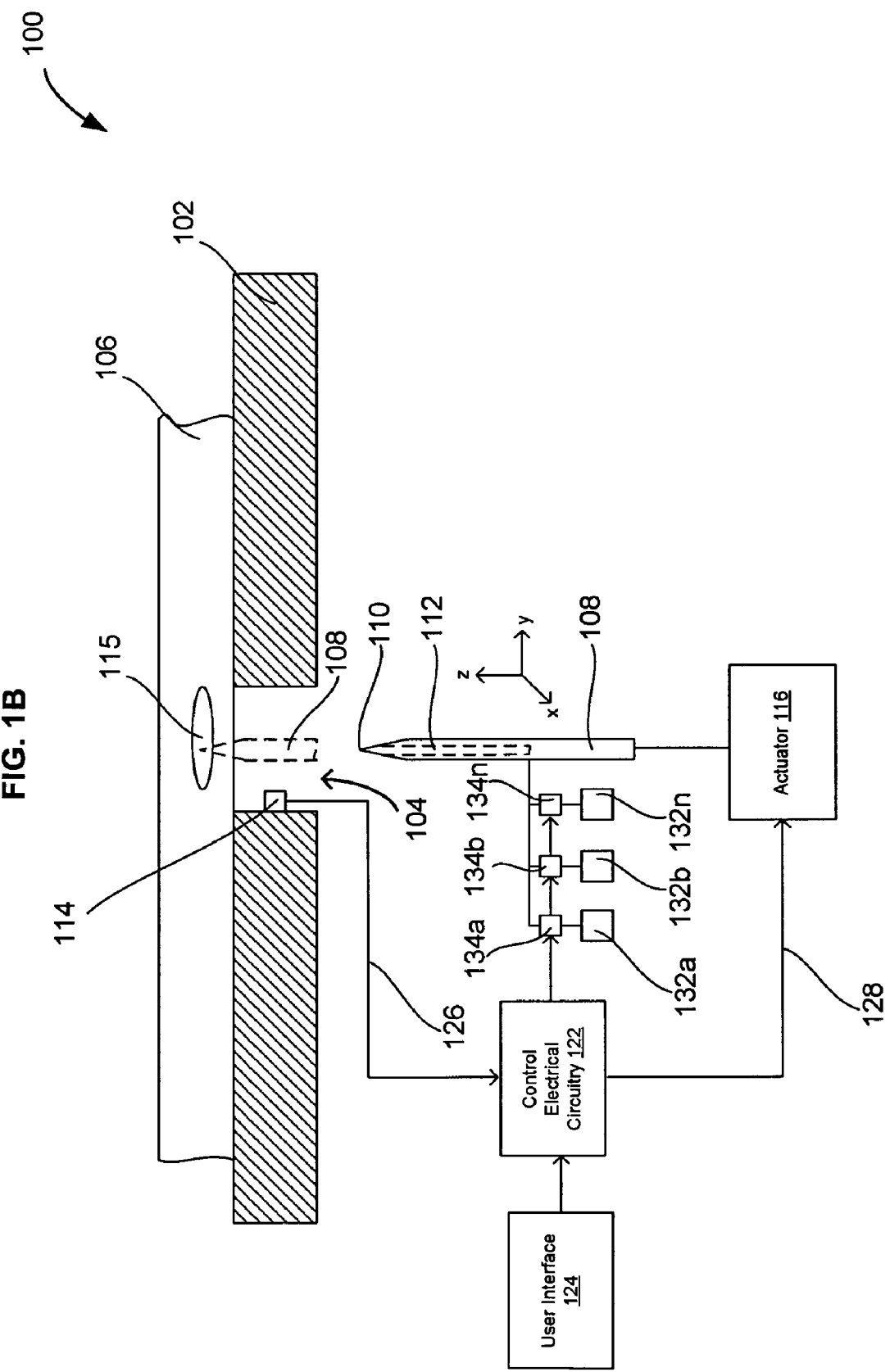
FIG. 1B is schematic diagram of an embodiment of a needle insertion system including multiple containers and corresponding pumps for delivering fluids to a living subject.

Referring to FIG. 1B, in an embodiment, a plurality of containers $132_a$-$132_n$ may be provided that hold different fluids (e.g., drugs, coagulants, nerve blocking agents, pain killers, etc.) to be delivered to the insertion-target region 115 or an exterior of the living subject via corresponding pumps $134_a$-$134_n$ pumping the fluids through and out of the passageway 112 of the moveable needle 108. The containers $132_a$-$132_n$ may be individually operably coupled to the corresponding pumps $134_a$-$134_n$ via fluid conduits and corresponding electronically controlled valves (not shown) that can be selectively opened and closed via a one or more control signals from the control electrical circuitry 122 to allow fluid to be selectively pumped to or from the containers $132_a$-$132_n$. For example, one or more of the containers $132_a$-$132_n$ may hold fluids to be pumped to the living subject, while one or more of the containers $132_a$-$132_n$ may serve as receptacles for receiving fluid pumped or drawn from the insertion-target region 115.

In operation, the machine-vision system 114 locates the insertion-target region 115 of the living subject and outputs one or more location-information signals 126 encoding location information about the insertion-target region 115 to the control electrical circuitry 122. In an embodiment, prior to or substantially simultaneously with insertion of the moveable needle 108 into the body part 106, a coagulant, a pain killer, or a nerve blocker optionally may be selectively pumped from a corresponding one of the containers $132_a$-$132_n$ using a corresponding one of the pumps $132_a$-$132_n$ (under control of the control electrical circuitry 122), out of the passageway 112 of the moveable needle 108, and onto skin or into tissue of the body part 106. Substantially simultaneously with or after delivery of the desired amount of fluid pumped out of the moveable needle 108, the control electrical circuitry 122 may direct the actuator 116 to selectively move and insert the moveable needle 108 into the insertion-target region 115 where additional fluids may be selectively delivered to the living subject or fluid may be drawn from insertion-target region 115 in accordance with the needle targeting instructions 128.

As an alternative to or in addition to selectively pumping specific fluids on or into the body part 106 prior to or with insertion of the moveable needle 108, in an embodiment, the control electrical circuitry 122 may direct one of the pumps $134_a$-$134_n$ to pump coagulant from one of the containers $132_a$-$132_n$ on or into the body part 106 of the living subject to promote coagulation of blood and prevent bleeding from the puncture made in the body part 106. In such an embodiment, the coagulant may be delivered to the body part 106 substantially simultaneously with the moveable needle 108 being withdrawn from the body part 106 or after the moveable needle 108 is withdrawn from the body part 106. In an aspect of such an embodiment, the control electrical circuitry 122 may instruct the actuator 116 to withdraw the moveable needle 108 at a selected withdrawal rate chosen to reduce bleeding from the punctured body part 106.

Figure 1C:
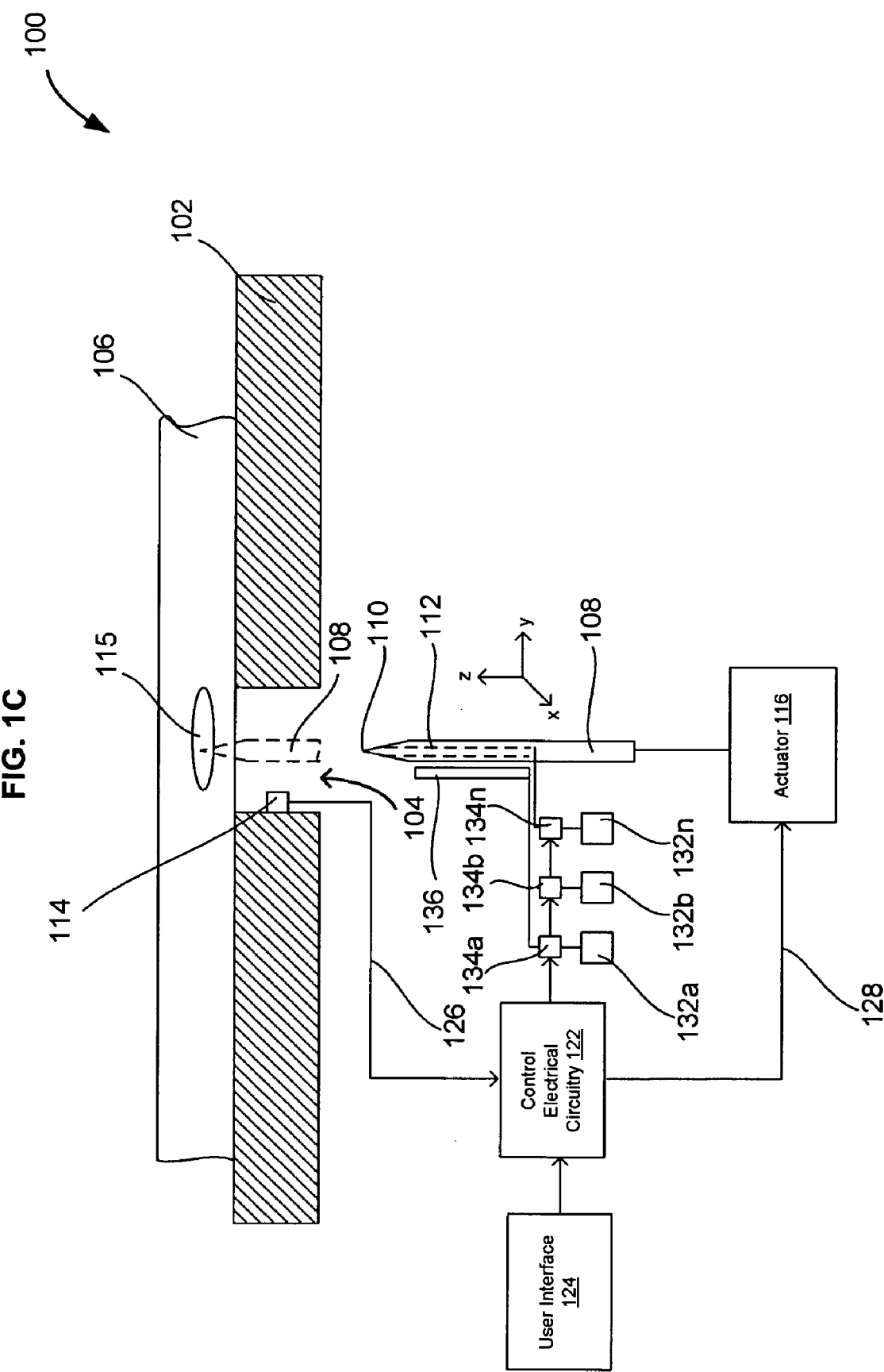
FIG. 1C is schematic diagram of an embodiment of a needle insertion system including a moveable needle and multiple containers and corresponding pumps for delivering fluids to a living subject through a dispensing device separate from the moveable needle.

As an alternative to one or more fluids being pumped from the containers $132_a$-$132_n$, through the passageway 112 formed in the moveable needle 108, and to the living subject, one or more fluids may be delivered using a dispensing device that is separate from the moveable needle 108. Referring to FIG. 1C, in an embodiment, a dispensing device 136 or other type of subject preparation device (e.g., a tube, a nozzle, or other fluid conduit or dispensing device) may be coupled to the actuator 116 to move only in the x and y direction and not in the z direction to prevent physical interference with the body part 106 during insertion of the moveable needle 108. In such an embodiment, one or more fluids may be selectively pumped through and out of the dispensing device 134 using, for example, the pumps $134_a$-$134_b$ and dispensed onto the exterior of the body part 106 before, during, or after insertion of the moveable needle 108 into the insertion-target region 115. Fluid (e.g., blood) from the insertion-target region 115 may be selectively pumped therefrom using the pump $134_n$ and into the container $132_n$. For example, at least one of a cleaning solution, a disinfecting agent, a pain killer, a coagulant, an anesthetizing agent, or a nerve blocker may be dispensed onto the body part 106 from the dispensing device 136 prior to the moveable needle 108 being inserted into the insertion-target region 115 to draw blood from the insertion-target region 115.

Figure 1D:
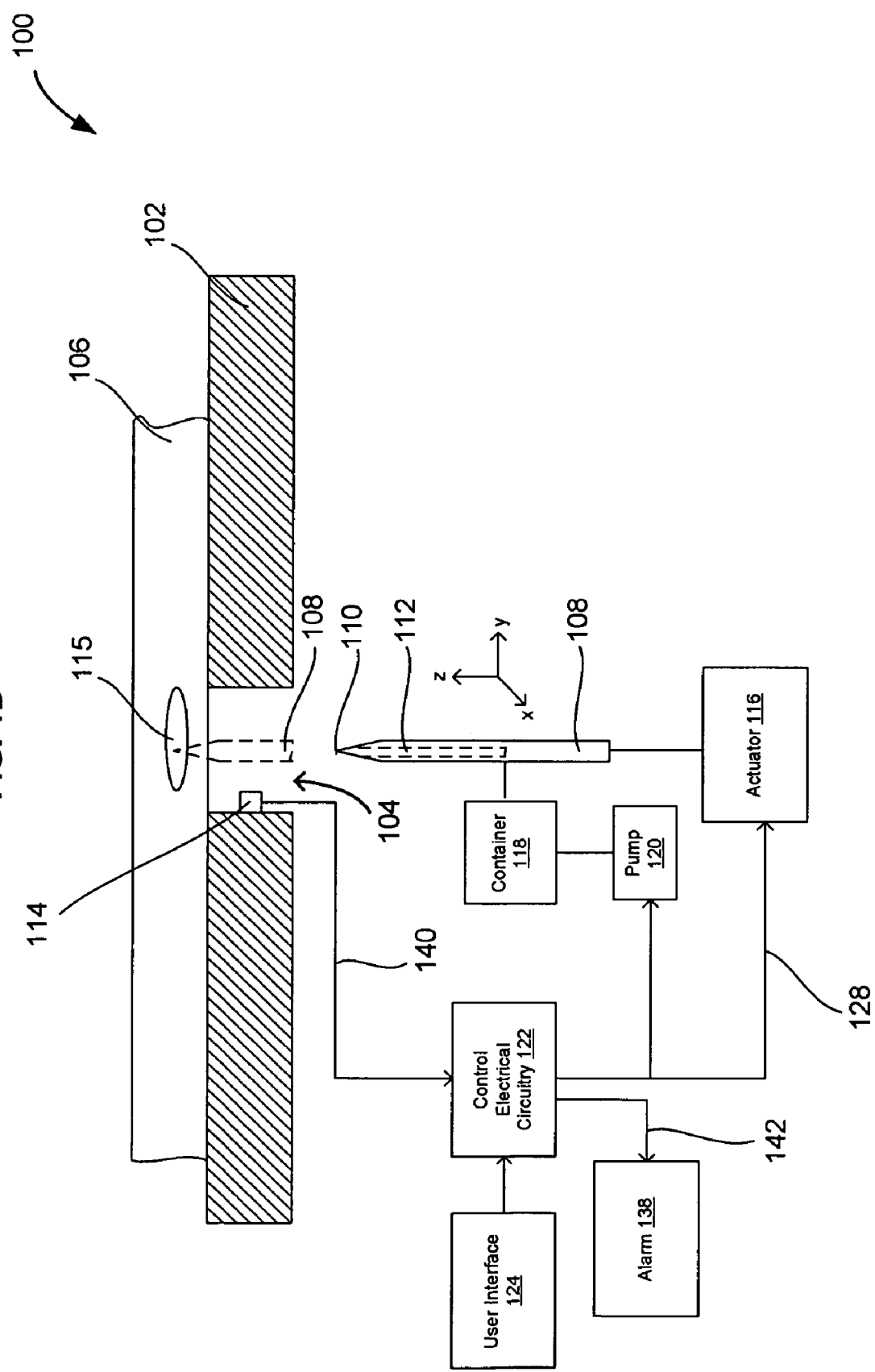
FIG. 1D is a schematic of the needle insertion system shown in FIG. 1A including an alarm for notifying a user when a machine-vision system of the system is unable to locate a suitable insertion-target region according to an embodiment.

In an embodiment, a needle insertion system may include an alarm that alerts the user (e.g., a medical technician or the living subject) when the machine-vision system 114 is not able to locate the insertion-target region 115. FIG. 1D is a schematic of the needle insertion system 100 including an alarm 138 coupled to the control electrical circuitry 122. In operation, the machine-vision system 114 outputs one or more notification signals 140 to the control electrical circuitry 122 when it is unable to locate the insertion-target region 115. One or more alarm signals 142 are output by the control electrical circuitry 122 to the alarm 138. In response to the one or more alarm signals 142, the alarm 138 may output a visible alarm that is perceivable by a human (e.g., a blinking light) or an audible noise. For example, the alarm 138 may include at least one of a buzzer or a light-emitting device (e.g., one or more light-emitting diodes). If the machine-vision system 114 is unable to locate the insertion-target region 115, the body part 106 may be moved so that a suitable insertion-target region may be detectable by the machine-vision system 114 through the through opening 104 of the support structure 102.

Figure 2:
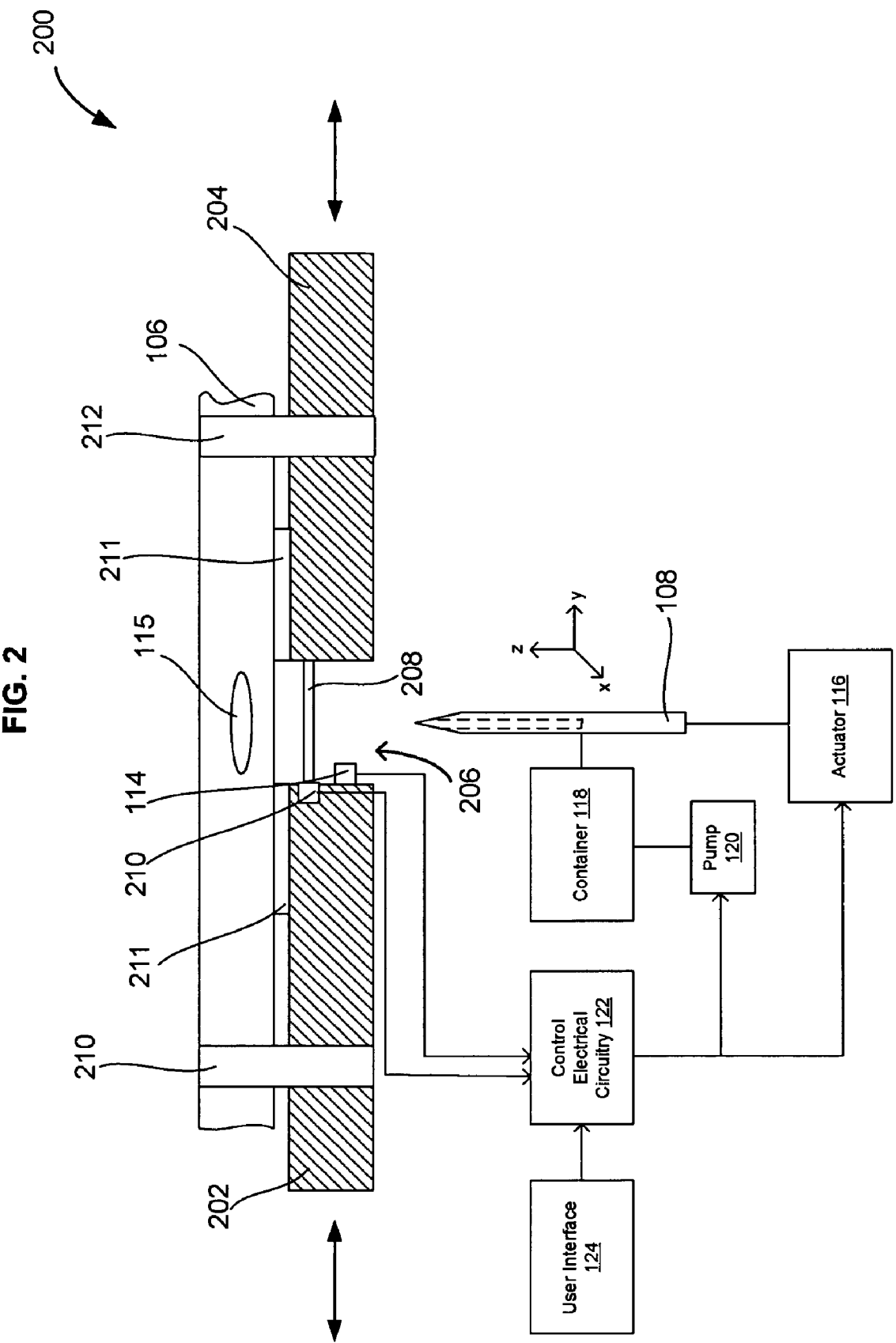
FIG. 2 is schematic diagram of an embodiment of a needle insertion system in which a support structure is configured to stretch the skin of a living subject prior to insertion of a moveable needle therein.

FIG. 2 is schematic diagram of an embodiment of a needle insertion system 200 in which a support structure is configured to stretch or compress the skin of a living subject prior to insertion of the moveable needle 108. The needle insertion system 200 includes many of the same components as the needle insertion system 100 shown in FIG. 1A. Therefore, in the interest of brevity, components in the needle insertion systems 100 and 200 that are identical to each other have been provided with the same reference numerals, and an explanation of their structure and function will not be repeated unless the components function differently in the needle insertion systems 100 and 200. However, it should be noted that the principles of the needle insertion system 200 may be employed with any of the embodiments described with respect to FIGS. 1A through 1D.

The needle insertion system 200 includes a support structure comprising a first and second support portions 202 and 204, respectively, that are spaced to define an opening 206 that provides access to the body part 106 of the living subject. For example, the first and second support portions 202 and 204 may each be moveable plates. The first and second support portions 202 and 204 are interconnected via a drive mechanism 208 (e.g., a screw-drive mechanism) driven by an actuator 210. The actuator 210 may be operably coupled to the control electrical circuitry 122. The first and second support portions 202 and 204, drive mechanism 208, and acuator 210 collectively form a subject preparation device configured to stretch the skin of the body part 106 to be punctured by the moveable needle 108 or apply pressure to puncture to help stop bleeding from the body part 106. For example, the drive mechanism 208 is configured to move the first and second support portions 202 and 204 apart to stretch the skin of the body part 106 to be punctured by the moveable needle 108 or together to apply pressure to puncture to help stop bleeding from the body part 106.

In the illustrated embodiment, pads 211 (e.g., rubber pads) may be mounted to the first and second support portions 202 and 204 to improve engagement between the first and second support portions 202 and 204 and the body part 106. However, the pads 211 may be omitted in other embodiments, and the body part 106 may be, for example, secured to the first and second support structures 202 and 204 with straps 212 or other mounting structure configured to temporarily secure at least the first and second portions 202 and 204, the moveable needle 108, and the actuator 116 on the body part 106 of the living subject.

In operation, the control electrical circuitry 122 may direct the actuator 210 to drive the drive mechanism 208 to move the first and second support structures 202 and 204 apart to stretch the skin of the body part 106 prior to the moveable needle 108 being controllably inserted into the insertion-target region 115 as performed in any of the embodiments discussed herein with respect to FIGS. 1A through 1D. In an embodiment, after removal of the moveable needle 108 from the body part 106, the control electrical circuitry 122 may move the first and second support structures 202 and 204 together apply a therapeutic amount of pressure to the puncture in the body part 106 created by insertion of the moveable needle 108 therein to help reduce or prevent bleeding.

In an embodiment, the needle insertion system 200 may be sized and configured as a self-contained handheld unit that may be enclosed in a suitable housing. In such an embodiment, the unit may mounted be to the living subject via the straps 212, adhesive, or other mounting structure and removed after the procedure is completed.

Figure 3:
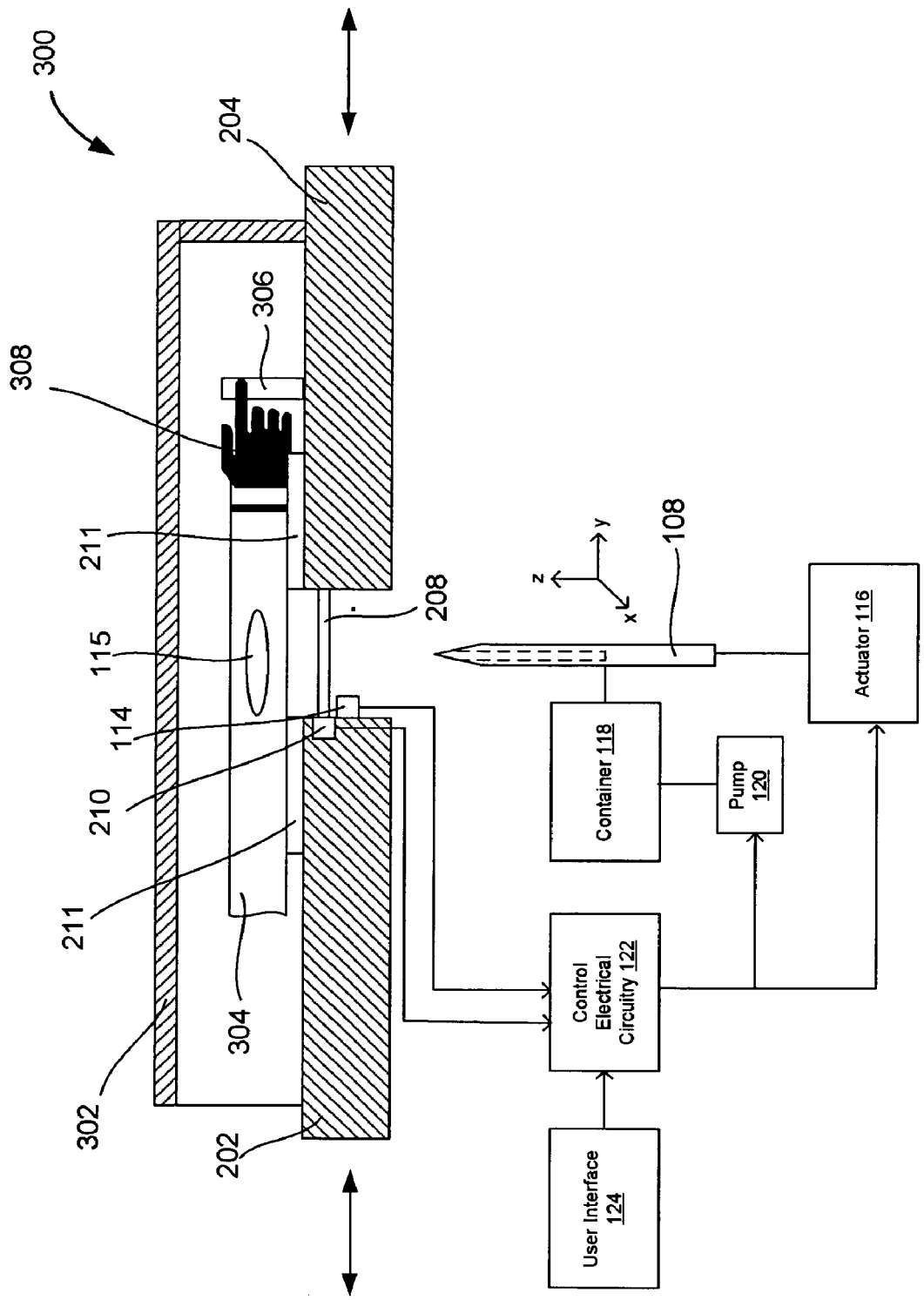
FIG. 3 is schematic diagram of an embodiment of a needle insertion system including an enclosure configured to conceal the moveable needle and other system components from a living subject.

FIG. 3 is schematic diagram of an embodiment of a needle insertion system 300 including an enclosure 302 configured to conceal the moveable needle 108 and other system components from the living subject. The needle insertion system 200 includes many of the same components as the needle insertion system 200 shown in FIG. 1A. Therefore, in the interest of brevity, components in the needle insertion systems 200 and 300 that are identical to each other have been provided with the same reference numerals, and an explanation of their structure and function will not be repeated unless the components function differently in the needle insertion systems 200 and 300. However, it should be noted that the principles of the needle insertion system 300 may be employed with any of the embodiments described with respect to FIGS. 1A through 1D.

The needle insertion system 300 may include an enclosure 302 movably mounted to the first and second support structures 202 and 204. The enclosure 302 at least partially conceals the moveable needle 108 from the view of the living subject to help ease anxiety in the living subject during needle insertion. In use, the living subject may insert their forearm 304 inside of the enclosure 302 and grip a shaft 306 mounted to the second support portion 204 with their hand 308 for comfort.

Figure 4:
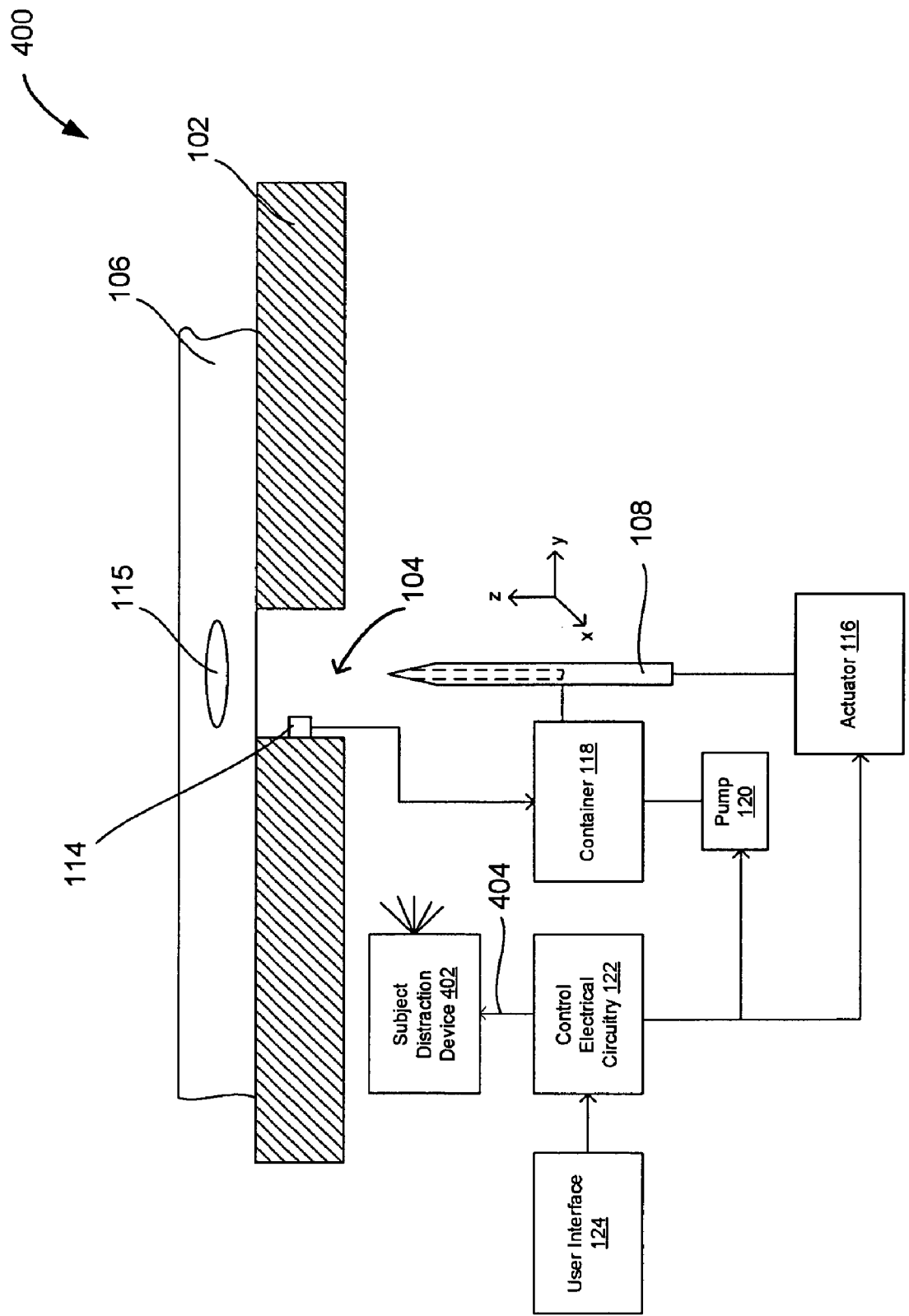
FIG. 4 is schematic diagram of an embodiment of a needle insertion system including a subject distraction device configured to distract a living subject prior to or during insertion of a moveable needle therein.

In an embodiment, any of the disclosed needle insertion systems may employ a subject distraction device configured to distract a living subject prior to or during insertion of a moveable needle of a needle insertion system. For example, FIG. 4 is schematic diagram of an embodiment of a needle insertion system 400 including a subject distraction device configured to distract the living subject prior to or during insertion of the moveable needle therein. The needle insertion system 400 includes many of the same components as the needle insertion system 100 shown in FIG. 1A. Therefore, in the interest of brevity, components in the needle insertion systems 100 and 400 that are identical to each other have been provided with the same reference numerals, and an explanation of their structure and function will not be repeated unless the components function differently in the needle insertion systems 100 and 400. However, it should be noted that the principles of the needle insertion system 400 may be employed with any of the embodiments described with respect to FIGS. 1A through 1D.

The needle insertion system 400 includes a subject distraction device 402 coupled to the control electrical circuitry 122. For example, the subject distraction device 402 may be a noise generation device (e.g., a horn, buzzer, or beeper) configured to generate a noise audible to the living subject or a visual distraction device (e.g., a bright flashing light-emitting diode array).

In operation, after the machine-vision system 114 has located the insertion-target region 115 or substantially simultaneously with the machine-vision system 114 locating the insertion-target region 115, the control electrical circuitry 122 outputs one or more signals 404 to the subject distraction device 402. The subject distraction device 402 outputs a loud noise or visual distraction in response to the one or more signals 404 sufficient to distract the user. After or substantially simultaneously with the subject distraction device 402 outputting a noise or visual effect to distract the living subject, the moveable needle 108 may be inserted into the insertion-target region 115 as performed in any of the embodiments described with respect to FIGS. 1A through 1D.

Figure 5:
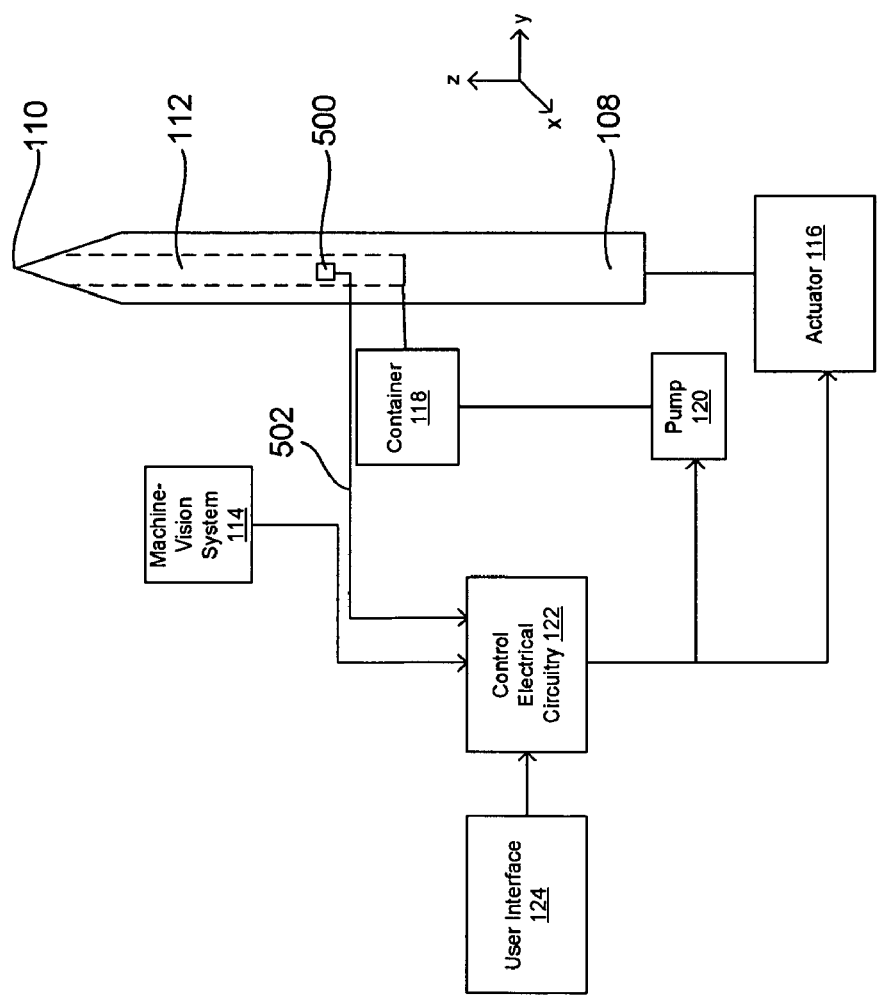
FIG. 5 is a schematic diagram of a moveable needle that may be operably associated with one or more sensors coupled to control electrical circuitry.

In any of the disclosed needle insertion systems embodiments, a needle insertion system may include one or more sensors operably associated with a moveable needle to sense one or more different operational parameters. For example, referring to FIG. 5, a sensor 500 may be operably associated with the moveable needle 108 of the needle insertion system 100 of FIG. 1A. In the illustrated embodiment, the sensor 500 may be disposed in the passageway 112 of the moveable needle 108 and configured to sense at least one of fluid flow drawn through the passageway 112 of the moveable needle 108 or the presence of blood in the passageway 112 of the moveable needle 108. The sensor 500 may output one or more sensing signals 502 in response to sensing such operational characteristics. In such an embodiment, the control electrical circuitry 122 may be configured to direct the actuator 116 to suspend further penetration of the moveable needle 108 into the living subject in response to the one or more sensing signals 502 output by the sensor 500.

In an embodiment, the sensor 500 may be a position sensor operably associated with the moveable needle 108 and configured to sense a position of the moveable needle 108 within the body part 106. The control electrical circuitry 122 may be configured to control movement of the moveable needle 108 in response to one or more sensing signals from the sensor 500 encoding a position of the moveable needle 108. For example, the sensor 500 may be an encoder, a linear variable differential transformer, or another suitable position sensor.

In an embodiment, the sensor 500 may be configured to sense the physical resistance of tissue of the body part 106 to penetration by or continued displacement in the living subject by the moveable needle 108. In such an embodiment, the sensor 500 may be a pressure transducer that is operably associated with the moveable needle 108 and configured to determine that amount of force required for the actuator 116 to continue penetration into the tissue of the body part 106.

FIG. 6 is schematic diagram of an embodiment of a needle insertion system 600 including a robotic arm having a moveable needle mounted thereto. The needle insertion system 600 includes a robotic arm 602 that is moveable in and about x, y, and z axes. The arm 602 is associated with an actuator 604a configured to drive the motion thereof. Control electrical circuitry 606 is coupled to the actuator 604a to control the operation thereof. A user interface 624 (e.g., a touchscreen, keypad, etc.) for user input may be coupled to the control electrical circuitry 606 to allow user to select various operational parameters for the arm 602 or other components of the needle insertion system 600.

The needle insertion system 600 further includes a moveable needle 608 moveably attached to an end of the arm 602. The moveable needle 608 may further be independently moveable in and about the x, y, z axes and driven by a needle actuator 604b coupled to the control electrical circuitry 606. A passageway 610 may be formed in the moveable needle 608 to allow fluid to flow in and out of the moveable needle 608. For example, a pump 612 may be in fluid communication with the passageway 610 and configured to draw fluid from a selected insertion-target region of a living subject 614 into a container 616.

The needle insertion system 600 also includes a machine-vision system 618 coupled to the control electrical circuitry 606. The machine-vision system 618 may be any of the previously described types of machine-vision systems. The machine-vision system is configured to determine when a living subject 614 is within operational range of the moveable needle 608, and further locate an insertion-target region in a body part of the living subject 614. The living subject 614 is within operational range of the moveable needle 108 when the arm 602 and moveable needle 608 are capable of moving independently or in concert to insert the moveable needle 608 into the located insertion-target region.

In operation, the machine-vision system 618 determines whether the living subject 614 is within operational range and, if so, locates an insertion-target region of the living subject 614. In response to one or more location-encoding signals from the machine-vision system 618, the control electrical circuitry 606 (automatically and without human intervention) directs the actuators 604a or 604b to move the moveable needle 608 into the insertion-target region located by the machine-vision system 618 and the pump 612 may draw fluid therefrom. Of course, the needle insertion system 600 may include one or more of the other features disclosed in other needle insertion system embodiments disclosed herein, such as being able to selectively dispense fluids on or in the living subject 614, distract the living subject 614 prior to or during insertion of the moveable needle 608, alert the living subject 614 when the machine-vision system 618 does not locate a suitable insertion-target region, among other features.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A needle insertion system, comprising:
    a moveable needle configured to be inserted into a living subject;
    a machine-vision system configured to locate on the living subject one or more punctured external locations in which the movable needle or another needle has been previously inserted and removed, and an insertion-target region different from the one or more punctured external locations;
    control electrical circuitry coupled to the machine-vision system to direct the machine-vision system to locate the insertion-target region, distinguish the insertion-target region from the one or more punctured external locations, and receive location information from the machine-vision system about the insertion-target region, the control electrical circuitry configured to output moveable needle targeting instructions; and
    an actuator coupled to the control electrical circuitry to receive the needle targeting instructions therefrom and coupled to the moveable needle, the actuator configured to move the moveable needle to the insertion-target region automatically in response to receiving the needle targeting instructions to thereby avoid the one or more punctured external locations.

2. The needle insertion system of claim 1, wherein the actuator is configured to, without human intervention after the moveable needle is positioned within operational range relative to the living subject, move the moveable needle to the insertion-target region located by the machine-vision system automatically in response to instructions from the control electrical circuitry.

3. The needle insertion system of claim 1, wherein the moveable needle includes a passageway configured to allow fluid to flow therethrough.

4. The needle insertion system of claim 1, further comprising:
at least one container holding fluid therein, the at least one container in fluid communication with the moveable needle; and
a pump configured to pump the fluid from the at least one container, and through and out of a passageway formed in the moveable needle.

5. The needle insertion system of claim 1, further comprising:
at least one container configured to hold fluid therein, the at least one container in fluid communication with the moveable needle; and
a pump configured to draw blood from the insertion-target region, through a passageway formed in the moveable needle, and into the at least one container.

6. The needle insertion system of claim 1, further comprising:
at least one container configured to hold fluid therein, the at least one container in fluid communication with the moveable needle; and
a suction device configured to draw blood from the insertion-target region, through a passageway formed in the moveable needle, and into the at least one container.

7. The needle insertion system of claim 1, wherein:
the control electrical circuitry is configured to direct the actuator to move the moveable needle to penetrate at least another location on the living subject that has not been previously penetrated by the moveable needle or the another needle.

8. The needle insertion system of claim 1, wherein the insertion-target region includes an internal insertion-target region disposed within the living subject, and wherein the machine-vision system is configured to locate the internal insertion-target region.

9. The needle insertion system of claim 8, wherein the internal insertion-target region includes at least one of an artery, a muscle, or a bone.

10. The needle insertion system of claim 1, wherein the insertion-target region includes external tissue of the living subject.

11. The needle insertion system of claim 1, wherein the machine-vision system includes an electronic camera.

12. The needle insertion system of claim 1, wherein the machine-vision system includes an ultrasonic imaging device, a visual-imaging device, an infrared-imaging device, an x-ray-imaging device, or a thermal-imaging device.

13. The needle insertion system of claim 1 wherein the control electrical circuitry is configured with a plurality of different force settings, and wherein the actuator is configured to bias the moveable needle with a force corresponding to a selected one of the plurality of different force settings.

14. The needle insertion system of claim 1, wherein the actuator includes at least one of a pneumatic actuator, a hydraulic actuator, a piezoelectric actuator, a linear actuator, a shape memory actuator, or an electro-mechanical actuator.

15. The needle insertion system of claim 1, further comprising a mounting structure configured to temporarily secure the moveable needle and the actuator to the living subject.

16. The needle insertion system of claim 15, wherein the mounting structure includes a moveable support structure configured to move the moveable needle into an operational position.

17. The needle insertion system of claim 15, wherein the mounting structure includes one or more straps configured to hold the moveable needle and the actuator on the living subject.

18. The needle insertion system of claim 15, wherein the mounting structure includes an adhesive.

19. The needle insertion system of claim 1, wherein the moveable needle, the machine-vision system, the control electrical circuitry, and the actuator are integrated into a hand-held unit.

20. The needle insertion system of claim 1, further comprising at least one sensor coupled to the control electrical circuitry and configured to sense at least one of fluid flow drawn through the moveable needle, position of the moveable needle within the living subject, tissue resistance of the living subject to the moveable needle, or presence of blood.

21. The needle insertion system of claim 20, wherein the control electrical circuitry is configured to control movement of the moveable needle in response to one or more sensing signals received from the at least one sensor.

22. The needle insertion system of claim 1, further comprising a subject preparation device configured to prepare a selected region of the living subject for insertion of the moveable needle therethrough.

23. The needle insertion system of claim 22, wherein the subject preparation device configured to dispense at least one of a cleaning agent, a pain killer, an anesthesia, a nerve blocker, or an antiseptic onto the selected region of the living subject.

24. The needle insertion system of claim 22, wherein the subject preparation device is configured to stretch or compress skin of the living subject in or near the insertion-target region.

25. The needle insertion system of claim 1, further comprising a robotic arm including the moveable needle mounted thereto, the robotic arm configured to move the moveable needle in response to instructions from the control electrical circuitry.

26. The needle insertion system of claim 1, further comprising an alarm configured to output a human perceivable indication to indicate that the machine-vision system is unable to locate the insertion-target region.

27. The needle insertion system of claim 1, further comprising a subject distraction device configured to distract the living subject prior to the moveable needle being inserted therein.

28. The needle insertion system of claim 27, wherein the subject distraction device includes a sound-generation device configured to output noise audible to the living subject prior to or during insertion of the moveable needle into the living subject.

29. The needle insertion system of claim 27, wherein the subject distraction device is configured to visually distract the living subject prior to or during insertion of the moveable needle into the living subject.

30. The needle insertion system of claim 1, further comprising:
a coagulant dispenser configured to dispense coagulant onto a region of the living subject; and
wherein the control electrical circuitry is configured to direct the coagulant dispenser to dispense the coagulant onto a region of the living subject that has been penetrated by the moveable needle.

31. The needle insertion system of claim 1, wherein the control electrical circuitry is configured to control a withdrawal rate of the moveable needle from the living subject.

32. The needle insertion system of claim 1, further comprising a coagulant dispenser configured to apply a therapeutic force to the region after the moveable needle has been withdrawn from the living subject.

33. The needle insertion system of claim 30, wherein the control electrical circuitry is configured to direct the coagulant dispenser to dispense the coagulant substantially simultaneously with withdrawal of the moveable needle from the living subject.

34. The needle insertion system of claim 1, wherein the control electrical circuitry is configured to correlate anatomical information viewed by and received from the machine-vision system with known anatomical data about the living subject.

35. The needle insertion system of claim 34, wherein the known anatomical information was determined using at least one of ultrasound imaging, x-ray imaging, magnetic resonance imaging, infrared imaging, visual imaging, or a computed tomography scan.

36. A needle insertion system, comprising:
   a single moveable needle configured to be inserted into a living subject;
   a machine-vision system configured to locate on the living subject one or more punctured external locations in which the movable needle or another needle has been previously inserted and removed, and an insertion-target region different from the one or more punctured external locations;
   control electrical circuitry coupled to the machine-vision system to receive location information therefrom about the insertion-target region, the control electrical circuitry configured to output moveable needle targeting instructions;
   an actuator coupled to the control electrical circuitry to receive the needle targeting instructions therefrom and coupled to the moveable needle, the actuator configured to move the moveable needle to the insertion-target region automatically in response to receiving the needle targeting instructions to thereby avoid the one or more punctured external locations; and
   a plurality of containers in fluid communication with the single moveable needle, each of the plurality of containers being configured and in fluid communication with the single moveable needle to either contain a fluid to be delivered to the living subject through the single moveable needle or receive a fluid drawn through the single moveable needle from the living subject.

37. The needle insertion system of claim 36, wherein the actuator is configured to, without human intervention after the single moveable needle is positioned within operational range relative to the living subject, move the single moveable needle to the insertion-target region located by the machine-vision system automatically in response to instructions from the control electrical circuitry.

38. The needle insertion system of claim 36, wherein the single moveable needle includes a passageway configured to allow fluid to flow therethrough.

39. The needle insertion system of claim 36, further comprising:
   a plurality of pumps, each of the plurality of pumps being associated with a corresponding one of the plurality of containers, each of the plurality of pumps being configured to pump the fluid from the corresponding one of the plurality of containers through and out of a passageway formed in the single moveable needle.

40. The needle insertion system of claim 36, further comprising:
   a plurality of pumps, each of the plurality of pumps being associated with a corresponding one of the plurality of containers, each of the plurality of pumps being configured to draw blood from the insertion-target region, through a passageway formed in the single moveable needle, and into the corresponding one of the plurality of containers.

41. The needle insertion system of claim 36, wherein the insertion-target region includes an internal insertion-target region disposed within the living subject, and wherein the machine-vision system is configured to locate the internal insertion-target region.

42. The needle insertion system of claim 41, wherein the internal insertion-target region includes at least one of an artery, a muscle, or a bone.

43. The needle insertion system of claim 36, wherein the insertion-target region includes external tissue of the living subject.

44. The needle insertion system of claim 36, wherein the machine-vision system includes an electronic camera.

45. The needle insertion system of claim 36, wherein the machine-vision system includes an ultrasonic imaging device, a visual-imaging device, an infrared-imaging device, an x-ray-imaging device, or a thermal-imaging device.

46. The needle insertion system of claim 36, wherein the control electrical circuitry is configured with a plurality of different force settings, and wherein the actuator is configured to bias the single moveable needle with a force corresponding to a selected one of the plurality of different force settings.

47. The needle insertion system of claim 36, wherein the actuator includes at least one of a pneumatic actuator, a hydraulic actuator, a piezoelectric actuator, a linear actuator, a shape memory actuator, or an electro-mechanical actuator.

48. The needle insertion system of claim 36, wherein the control electrical circuitry is configured to control a withdrawal rate of the single moveable needle from the living subject.

49. The needle insertion system of claim 36, wherein the control electrical circuitry is configured to correlate anatomical information viewed by and received from the machine-vision system with known anatomical data about the living subject.

50. The needle insertion system of claim 49, wherein the known anatomical information was determined using at least one of ultrasound imaging, x-ray imaging, magnetic resonance imaging, infrared imaging, visual imaging, or a computed tomography scan.

* * * * *